(12) United States Patent
Janzig et al.

(10) Patent No.: US 8,457,744 B2
(45) Date of Patent: Jun. 4, 2013

(54) LOW-PROFILE IMPLANTABLE MEDICAL DEVICE

(75) Inventors: Darren A. Janzig, Centerville, MN (US); Carl D. Wahlstrand, Lino Lakes, MN (US); Paulette C. Olson, Eagan, MN (US); Robert M. Skime, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 1277 days.

(21) Appl. No.: 10/730,877

(22) Filed: Dec. 9, 2003

(65) Prior Publication Data

US 2004/0176815 A1 Sep. 9, 2004

Related U.S. Application Data

(60) Provisional application No. 60/431,854, filed on Dec. 9, 2002, provisional application No. 60/471,262, filed on May 16, 2003, provisional application No. 60/503,945, filed on Sep. 20, 2003, provisional application No. 60/503,946, filed on Sep. 20, 2003, provisional application No. 60/507,857, filed on Oct. 1, 2003.

(51) Int. Cl.
*A61N 1/08* (2006.01)

(52) U.S. Cl.
USPC .............................................. 607/36; 607/45

(58) Field of Classification Search
USPC ............. 607/45, 46, 62, 36; 623/10; 437/874; 600/476
See application file for complete search history.

(56) References Cited

U.S. PATENT DOCUMENTS

| | | | |
|---|---|---|---|
| 3,690,325 | A | 9/1972 | Kenny |
| 3,720,874 | A | 3/1973 | Gorcik et al. |
| 3,724,467 | A | 4/1973 | Avery et al. |
| 3,888,260 | A | 6/1975 | Fischell |
| 3,913,587 | A | 10/1975 | Newash |

(Continued)

FOREIGN PATENT DOCUMENTS

| | | |
|---|---|---|
| DE | 3940632 | 12/1990 |
| EP | 1 145 735 A2 | 10/2001 |

(Continued)

OTHER PUBLICATIONS

Answers.com, www.answers.com, defined: discrete components, acessed on Mar. 2, 2007.*

(Continued)

*Primary Examiner* — Niketa Patel
*Assistant Examiner* — Alyssa M Alter
(74) *Attorney, Agent, or Firm* — Shumaker & Sieffert, P.A.

(57) ABSTRACT

Components of an implantable medical device are arranged to facilitate a low-profile housing. A circuit board within the housing carries integrated circuits and discrete components. In some embodiments, the integrated circuits and discrete components are located on first and second opposing surfaces of the circuit board, respectively. In some embodiments, the implantable medical device is implanted on a cranium of a patient and the housing is concave such that it substantially conforms to the cranium. In such embodiments, the integrated circuits and/or discrete components can be arranged on the circuit board according to height to better conform to the concavity of the housing. In some embodiments, the implantable medical device includes a telemetry coil that is positioned within the housing such that it occupies space that cannot be practically occupied by the circuit board.

60 Claims, 6 Drawing Sheets

U.S. PATENT DOCUMENTS

| | | | |
|---|---|---|---|
| 3,926,198 A | 12/1975 | Kolenik | |
| 4,013,081 A | 3/1977 | Kolenik | |
| 4,040,412 A | 8/1977 | Sato | |
| 4,094,321 A | 6/1978 | Muto | |
| 4,266,552 A | 5/1981 | Dutcher et al. | |
| 4,328,813 A | 5/1982 | Ray | |
| 4,399,819 A | 8/1983 | Cowdery | |
| 4,399,820 A | 8/1983 | Wirtzfeld et al. | |
| 4,499,907 A | 2/1985 | Kallok et al. | |
| 4,616,655 A | 10/1986 | Weinberg et al. | |
| 4,911,178 A | 3/1990 | Neal | |
| 4,928,696 A | 5/1990 | Henderson et al. | |
| 4,934,368 A | 6/1990 | Lynch | |
| 4,969,899 A | 11/1990 | Cox, Jr. | |
| 4,972,846 A | 11/1990 | Owens et al. | |
| 5,085,644 A | 2/1992 | Watson et al. | |
| 5,116,345 A | 5/1992 | Jewell et al. | |
| 5,144,946 A | 9/1992 | Weinberg et al. | |
| 5,197,332 A | 3/1993 | Shennib | |
| 5,207,218 A | 5/1993 | Carpentier et al. | |
| 5,220,929 A | 6/1993 | Marquit | |
| 5,252,090 A | 10/1993 | Giurtino et al. | |
| 5,271,397 A | 12/1993 | Seligman et al. | |
| 5,312,440 A | 5/1994 | Hirschberg et al. | |
| 5,314,451 A | 5/1994 | Mulier | |
| 5,314,453 A | 5/1994 | Jeutter | |
| 5,433,734 A | 7/1995 | Stokes et al. | |
| 5,455,999 A | 10/1995 | Owens et al. | |
| 5,456,698 A | 10/1995 | Byland et al. | |
| 5,480,416 A | 1/1996 | Garcia et al. | |
| 5,489,225 A | 2/1996 | Julian | |
| 5,554,194 A | 9/1996 | Sanders | |
| 5,562,715 A | 10/1996 | Czura et al. | |
| 5,571,148 A | 11/1996 | Loeb et al. | |
| 5,613,935 A | 3/1997 | Jarvik | |
| 5,638,832 A | 6/1997 | Singer et al. | |
| 5,645,586 A | 7/1997 | Meltzer | |
| 5,674,260 A * | 10/1997 | Weinberg | 607/36 |
| 5,678,559 A | 10/1997 | Drakulic | |
| 5,702,430 A | 12/1997 | Slimon et al. | |
| 5,741,313 A | 4/1998 | Nason et al. | |
| 5,755,743 A | 5/1998 | Volz et al. | |
| 5,769,874 A | 6/1998 | Dahlberg | |
| 5,776,169 A | 7/1998 | Schroeppel | |
| 5,800,535 A * | 9/1998 | Howard, III | 623/10 |
| 5,814,095 A | 9/1998 | Müller et al. | |
| 5,843,150 A | 12/1998 | Adams et al. | |
| 5,873,899 A | 2/1999 | Stutz, Jr. et al. | |
| 5,876,424 A | 3/1999 | O'Phelan et al. | |
| 5,895,414 A | 4/1999 | Sanchez-Zambrano | |
| 5,896,647 A | 4/1999 | Shkuratoff | |
| 5,919,215 A | 7/1999 | Haeg et al. | |
| 5,935,154 A | 8/1999 | Westlund | |
| 5,941,905 A | 8/1999 | Single | |
| 5,941,906 A | 8/1999 | Barreras, Sr. et al. | |
| 5,954,751 A * | 9/1999 | Chen et al. | 607/5 |
| 5,958,088 A | 9/1999 | Vu et al. | |
| 5,984,859 A | 11/1999 | Lesinski | |
| 5,991,664 A | 11/1999 | Seligman | |
| 6,006,124 A | 12/1999 | Fischell et al. | |
| 6,016,449 A | 1/2000 | Fischell et al. | |
| 6,016,593 A | 1/2000 | Kyrstein | |
| 6,044,304 A | 3/2000 | Baudino | |
| 6,052,623 A | 4/2000 | Fenner et al. | |
| 6,061,593 A | 5/2000 | Fischell et al. | |
| 6,067,474 A | 5/2000 | Schulman et al. | |
| 6,091,979 A | 7/2000 | Madsen | |
| 6,128,538 A | 10/2000 | Fischell et al. | |
| 6,131,581 A | 10/2000 | Leysieffer et al. | |
| 6,134,474 A | 10/2000 | Fischell et al. | |
| 6,162,487 A | 12/2000 | Darouiche | |
| 6,168,580 B1 | 1/2001 | Yardley | |
| 6,176,879 B1 | 1/2001 | Reischl et al. | |
| 6,205,358 B1 | 3/2001 | Haeg et al. | |
| 6,214,032 B1 | 4/2001 | Loeb et al. | |
| 6,218,016 B1 | 4/2001 | Tedeschi et al. | |
| 6,230,049 B1 | 5/2001 | Fischell et al. | |
| 6,248,080 B1 | 6/2001 | Miesel et al. | |
| 6,259,951 B1 | 7/2001 | Kuzma et al. | |
| 6,263,225 B1 | 7/2001 | Howard, III | |
| 6,266,556 B1 | 7/2001 | Ives et al. | |
| 6,269,266 B1 | 7/2001 | Leysieffer | |
| 6,272,382 B1 | 8/2001 | Faltys et al. | |
| 6,308,101 B1 | 10/2001 | Faltys et al. | |
| 6,324,428 B1 | 11/2001 | Weinberg et al. | |
| 6,327,502 B1 | 12/2001 | Johansson et al. | |
| 6,330,468 B1 * | 12/2001 | Scharf | 600/476 |
| 6,354,299 B1 | 3/2002 | Fischell et al. | |
| 6,356,792 B1 | 3/2002 | Zonenshayn et al. | |
| 6,358,281 B1 | 3/2002 | Berrang et al. | |
| 6,360,122 B1 | 3/2002 | Fischell et al. | |
| 6,405,079 B1 | 6/2002 | Ansarinia | |
| 6,427,086 B1 | 7/2002 | Fischell et al. | |
| 6,436,422 B1 | 8/2002 | Trogolo et al. | |
| 6,445,956 B1 * | 9/2002 | Laird et al. | 607/61 |
| 6,456,886 B1 | 9/2002 | Howard et al. | |
| 6,480,743 B1 | 11/2002 | Kirkpatrick et al. | |
| 6,490,486 B1 | 12/2002 | Bradley | |
| 6,516,227 B1 * | 2/2003 | Meadows et al. | 607/46 |
| 6,517,476 B1 | 2/2003 | Bedoya et al. | |
| 6,537,200 B2 | 3/2003 | Leysieffer et al. | |
| 6,554,762 B2 | 4/2003 | Leysieffer | |
| 6,560,486 B1 | 5/2003 | Osorio et al. | |
| 6,565,503 B2 | 5/2003 | Leysieffer et al. | |
| 6,567,703 B1 | 5/2003 | Thompson et al. | |
| 6,575,894 B2 | 6/2003 | Leysieffer et al. | |
| 6,597,954 B1 * | 7/2003 | Pless et al. | 607/62 |
| 6,618,623 B1 | 9/2003 | Pless et al. | |
| 6,626,680 B2 * | 9/2003 | Ciurzynski et al. | 439/874 |
| 6,648,914 B2 | 11/2003 | Berrang et al. | |
| 6,671,544 B2 | 12/2003 | Baudino | |
| 6,721,602 B2 | 4/2004 | Engmark et al. | |
| 6,726,678 B1 | 4/2004 | Nelson et al. | |
| 6,788,974 B2 | 9/2004 | Bardy et al. | |
| 6,805,998 B2 | 10/2004 | Jenson et al. | |
| 6,882,881 B1 | 4/2005 | Lesser et al. | |
| 6,899,976 B2 | 5/2005 | Larson et al. | |
| 6,963,780 B2 | 11/2005 | Ruben et al. | |
| 6,977,124 B2 | 12/2005 | Probst et al. | |
| 7,010,351 B2 | 3/2006 | Firlik et al. | |
| 7,103,415 B2 | 9/2006 | Probst et al. | |
| 7,107,097 B2 | 9/2006 | Stern et al. | |
| 7,110,819 B1 | 9/2006 | O'Hara | |
| 7,212,864 B2 | 5/2007 | Wahlstrand et al. | |
| 7,242,982 B2 | 7/2007 | Singhal et al. | |
| 7,263,401 B2 | 8/2007 | Scott et al. | |
| 2001/0033953 A1 | 10/2001 | Takeuchi et al. | |
| 2001/0051819 A1 | 12/2001 | Fischell et al. | |
| 2002/0002390 A1 | 1/2002 | Fischell et al. | |
| 2002/0013612 A1 | 1/2002 | Whitehurst | |
| 2002/0019669 A1 | 2/2002 | Berrang et al. | |
| 2002/0042634 A1 | 4/2002 | Bardy et al. | |
| 2002/0051550 A1 | 5/2002 | Leysieffer | |
| 2002/0068958 A1 | 6/2002 | Bardy et al. | |
| 2002/0087201 A1 | 7/2002 | Firlik et al. | |
| 2002/0099412 A1 | 7/2002 | Fischell et al. | |
| 2002/0103510 A1 | 8/2002 | Bardy et al. | |
| 2002/0107546 A1 | 8/2002 | Ostroff et al. | |
| 2002/0161403 A1 | 10/2002 | Meadows et al. | |
| 2002/0165588 A1 | 11/2002 | Fraley et al. | |
| 2003/0004428 A1 | 1/2003 | Pless et al. | |
| 2003/0004546 A1 | 1/2003 | Casey | |
| 2003/0040781 A1 | 2/2003 | Sunderland et al. | |
| 2003/0073972 A1 | 4/2003 | Rosenman et al. | |
| 2003/0085684 A1 | 5/2003 | Tsukamoto et al. | |
| 2003/0088294 A1 | 5/2003 | Gesotti | |
| 2003/0109903 A1 | 6/2003 | Berrang et al. | |
| 2003/0120320 A1 | 6/2003 | Solom | |
| 2003/0125786 A1 | 7/2003 | Gliner et al. | |
| 2003/0130706 A1 | 7/2003 | Sheffield et al. | |
| 2003/0171787 A1 | 9/2003 | Money et al. | |
| 2003/0204229 A1 | 10/2003 | Stokes | |
| 2004/0082977 A1 * | 4/2004 | Engmark et al. | 607/36 |
| 2004/0102828 A1 | 5/2004 | Lowry et al. | |
| 2004/0176815 A1 | 9/2004 | Janzig et al. | |
| 2004/0181263 A1 | 9/2004 | Balzer et al. | |
| 2004/0186528 A1 | 9/2004 | Ries et al. | |

| | | | |
|---|---|---|---|
| 2005/0033378 | A1 | 2/2005 | Sheffield et al. |
| 2005/0070971 | A1 | 3/2005 | Fowler et al. |
| 2005/0075679 | A1 | 4/2005 | Gliner et al. |
| 2006/0116743 | A1 | 6/2006 | Gibson et al. |
| 2006/0129205 | A1 | 6/2006 | Boveja et al. |

FOREIGN PATENT DOCUMENTS

| | | |
|---|---|---|
| EP | 1 145 736 A2 | 10/2001 |
| GB | 1 161 579 | 8/1969 |
| WO | WO 92/20402 | 11/1992 |
| WO | WO 00/13743 | 3/2000 |
| WO | WO 01/10369 | 2/2001 |
| WO | WO 01/28622 | 4/2001 |
| WO | WO 01/39830 | 6/2001 |
| WO | WO 01/41858 | 6/2001 |
| WO | WO 01/60450 | 8/2001 |
| WO | WO 01/97906 | 12/2001 |
| WO | WO 02/05590 | 1/2002 |
| WO | WO 02/056637 | 7/2002 |
| WO | WO 03/026739 | 4/2003 |
| WO | WO 03/076012 | 9/2003 |
| WO | WO 2004/043536 | 5/2004 |
| WO | 2004/052459 A1 | 6/2004 |
| WO | WO 2004/052458 | 6/2004 |

OTHER PUBLICATIONS

U.S. Appl. No. 10/731,868, filed Dec. 9, 2003, entitled "Implantation of Low-Profile Implantable Medical Device."

U.S. Appl. No. 10/731,699, filed Dec. 9, 2003, entitled "Coupling Module of a Modular Implantable Medical Device."

U.S. Appl. No. 10/730,873, filed Dec. 9, 2003, entitled "Overmold for a Modular Implantable Medical Device."

U.S. Appl. No. 10/731,881, filed Dec. 9, 2003, entitled "Reducing Relative Intermodule Motion in a Modular Implantable Medical Device."

U.S. Appl. No. 10/730,878, filed Dec. 9, 2003, entitled "Lead Interconnect Module of a Modular Implantable Medical Device."

U.S. Appl. No. 10/731,867, filed Dec. 9, 2003, entitled "Concavity of an Implantable Medical Device."

U.S. Appl. No. 10/731,638, filed Dec. 9, 2003, entitled "Modular Implantable Medical Device."

U.S. Appl. No. 10/731,869, filed Dec. 9, 2003, entitled "Modular Implantable Medical Device."

"Surgical Process," Animation Screenshots from http://www.cochlearamerica.com/800.asp, 7 pgs.

"Candidates Brochure," http://www.cochlearamerica.com/pdfs/candidatebrochglobal.pdf, 14 pgs.

"Nucleus 24 Contour," http://www.cochlearamericas.com/568.asp, 2 pgs.

"Nucleus 24 M," http://www.cochlearamericas.com/372.asp, 1 pg.

"Nucleus 24 K," http://www.cochlearamericas.com/371.asp, 1 pg.

"Nucleus 24 Double Array," http://www.cochlearamericas.com/370.asp, 1 pg.

"Nucleus 24 ABI: Auditory Brainstem Implant," http://www.cochlearamericas.com/373.asp, 2 pgs.

"Nucleus Speech Processors," http://www.cochlearamericas.com/629.asp, 1 pg.

"Sprint: body worn speech processor," http://www.cochlearamericas.com/1010.asp, 1 pg.

"Cochlear," http://www.cochlearamericas.com/Recipients/978.asp, 3 pgs.

"Research and Development," http://www.cochlearamericas.com/384.asp, 1 pg, (last printed Feb. 3, 2004).

"The World Leader in cochlear implants—revolutionizing hearing for adults and infants," http://www.cochlear.com, 1 pg. (last printed Feb. 3, 2004).

"Cochlear: innovator of the Nucleus 3 cochlear implant system," http://www.cochlearamericas.com, 1 pg. (last printed Feb. 3, 2004).

"What is a Cochlear Implant," http://www.cochlearamericas.com/What/161.asp, 1 pg. (last printed Feb. 3, 2004).

"ESPrit 30 Speech Processor," http://www.cochlearamericas.com/591.asp, 2 pgs. (last printed Feb. 3, 2004).

"Nucleus 3 System," http://www.cochlearamericas.com/Products/465.asp, 1 pg. (last printed Feb. 3, 2004).

"Internal Components: Nucleus 24 Cochlear Implants," http://www.cochlearamericas.com/374.asp, 1 pg. (last printed Feb. 3, 2004).

Notification of Transmittal of the International Search Report dated May 11, 2004, International Application No. PCT/US03/38927.

Written Opinion dated Dec. 16, 2004, International Application No. PCT/US03/38927.

Notification of Transmittal of the International Preliminary Examination Report dated Apr. 11, 2005, International Application No. PCT/US03/38927.

U.S. Appl. No. 10/837,319, filed Apr. 30, 2004, entitled "Implantable Medical Device With Anti-Infection Agent."

U.S. Appl. No. 10/835,527, filed Apr. 29, 2004, entitled "Implantation of Implantable Medical Device".

U.S. Appl. No. 10/835,232, filed Apr. 29, 2004, entitled "Explanation of Implantable Medical Device."

U.S. Appl. No. 10/835,233, filed Apr. 29, 2004, entitled "Implantable Medical Device With a Nonhermetic Battery."

U.S. Appl. No. 10/835,548, filed Apr. 29, 2004, entitled "Headset Recharger for Cranially Implantable Medical Devices."

U.S. Appl. No. 10/835,245, filed Apr. 29, 2004, entitled "Battery Housing Configuration."

U.S. Appl. No. 10/837,276, filed Apr. 30, 2004, entitled "Implantable Medical Device With Lubricious Material."

* cited by examiner

LOW-PROFILE IMPLANTABLE MEDICAL DEVICE

This application claims the benefit of:
1. U.S. Provisional Application entitled "CRANIAL NEUROSTIMULATOR AND METHOD," Ser. No. 60/431,854, filed on Dec. 9, 2002;
2. U.S. Provisional Application entitled "IMPLANTABLE CRANIAL MEDICAL DEVICES AND METHODS," Ser. No. 60/471,262, filed on May 16, 2003;
3. U.S. Provisional Application entitled "IMPLANTABLE CRANIAL MEDICAL DEVICES AND METHODS," Ser. No. 60/503,945, filed on Sep. 20, 2003;
4. U.S. Provisional Application entitled "IMPLANTABLE CRANIAL MEDICAL DEVICES AND METHODS," Ser. No. 60/503,946, filed on Sep. 20, 2003; and
5. U.S. Provisional Application entitled "Thin Neuro Stimulation System, Device and Method," Ser. No. 60/507,857, filed on Oct. 1, 2003.

The entire content of each of these U.S. Provisional Applications is incorporated herein by reference.

The following and commonly-assigned U.S. Patent Applications, filed on even date herewith, are also incorporated herein by reference in their entirety:
1. U.S. patent application Ser. No. 10/731,867, entitled "CONCAVITY OF AN IMPLANTABLE MEDICAL DEVICE," by Carl D. Wahlstrand et al., and filed Dec. 9, 2003, which issued as U.S. Pat. No. 7,529,586 on May 5, 2009;
2. U.S. patent application Ser. No. 10/731,868 entitled "IMPLANTATION OF LOW-PROFILE IMPLANTABLE MEDICAL DEVICE," by Ruchika Singhal et al., and filed Dec. 9, 2003, which published as U.S. Patent Application Publication No. 2004/0173221 on Sep. 9, 2004;
3. U.S. patent application Ser. No. 10/731,699 entitled "COUPLING MODULE OF A MODULAR IMPLANTABLE MEDICAL DEVICE," by Darren A. Janzig et al., and filed Dec. 9, 2003, which issued as U.S. Pat. No. 7,848,817 on Dec. 7, 2010;
4. U.S. patent application Ser. No. 10/730,873 entitled "OVERMOLD FOR A MODULAR IMPLANTABLE MEDICAL DEVICE," by Ruchika Singhal et al., and filed Dec. 9, 2003, which issued as U.S. Pat. No. 7,242,982 on Jul. 10, 2007;
5. U.S. patent application Ser. No. 10/731,881 entitled "REDUCING RELATIVE INTERMODULE MOTION IN A MODULAR IMPLANTABLE MEDICAL DEVICE," by Carl D. Wahlstrand et al., and filed Dec. 9, 2003, which issued as U.S. Pat. No. 7,392,089 on Jun. 24, 2008;
6. U.S. patent application Ser. No. 10/730,878 entitled "LEAD CONNECTION MODULE OF A MODULAR IMPLANTABLE MEDICAL DEVICE," by Ruchika Singhal et al., and filed Dec. 9, 2003, which published as U.S. Patent Application Publication No. 2004/0176816 on Sep. 9, 2004;
7. U.S. patent application Ser. No. 10/731,869 entitled "MODULAR IMPLANTABLE MEDICAL DEVICE," by Carl D. Wahlstrand et al., and filed Dec. 9, 2003, which published as U.S. Patent Application Publication No. 2004/0176818 on Sep. 9, 2004; and
8. U.S. patent application Ser. No. 10/731,638 entitled "MODULAR IMPLANTABLE MEDICAL DEVICE," Carl D. Wahlstrand et al., filed Dec. 9, 2003, which issued as U.S. Pat. No. 7,212,864 on May 1, 2007.

TECHNICAL FIELD

The invention relates to medical devices, and more particularly, to implantable medical devices that deliver therapy to and/or monitor a patient.

BACKGROUND

Depending on the application for which they are implanted in a patient, implantable medical devices (IMDs) may include a variety of electrical and/or mechanical components. Typically, an IMD includes a rigid housing that houses all of its components, which are generally fragile, to protect the components from forces to which they would otherwise be exposed when implanted within the human body. In order to avoid potentially harmful interactions between the components and bodily fluids, e.g., corrosion, IMD housings are typically hermetically sealed. Many IMD housings are fabricated from Titanium because of its desirable rigidity and biocompatibility.

The size and shape of an IMD housing is dependant on the sizes and shapes of the components of the IMD. Large components common to most IMDs include a battery, a telemetry coil, and a circuit board that carries digital circuits, e.g., integrated circuit chips and/or a microprocessor, and analog circuit components. Attempts have been made to reduce the size of the IMD housing by reducing the size of these components, changing the shape of these components, and organizing these components within the IMD housing to avoid empty space within the housing. Despite these efforts to reduce the size of IMD housings, the size, shape and rigidity of IMD housings still greatly limits the locations within the human body where an IMD can be practically implanted.

Due to these limitations, an IMD is typically implanted within the abdomen, upper pectoral region, or subclavicular region of a patient. Leads or catheters must be used in order to deliver therapy or monitor a physiological parameter at a location of the body other than where the IMD is implanted. Implantation and positioning of leads and catheters can be difficult and time-consuming from the perspective of a surgeon, particularly where the IMD is located a significant distance from the treatment or monitoring site. Moreover, the increased surgical time, increased surgical trauma, and increased amount of implanted material associated with the use of leads and catheters can increase the risk to the patient of complications associated with the implantation of an IMD.

For example, IMDs that are used to treat or monitor the brain, e.g., to deliver deep brain stimulation (DBS) therapy, are implanted some distance away from the brain, e.g., within the subclavicular region of patients. The long leads that connect the implantable medical device to electrodes implanted within the brain require tunneling under the scalp and the skin of the neck, thereby requiring increased surgery and a prolonged amount of time under general anesthesia during the implant procedure, as well as increased recovery time. In some cases, tunneling the leads under the scalp and skin of the neck requires an additional surgical procedure under general anesthesia. The lengthy tract along the leads is more susceptible to infection, and the leads can erode the overlying scalp, forcing removal so that the scalp can heal. Further, the long leads running under the scalp and through the neck are more susceptible to fracture due to torsional and other forces caused by normal head and neck movements.

SUMMARY

In general, the invention is directed to an implantable medical device with a low-profile housing. In particular, the invention is directed to arrangements of components of the implantable medical device such that the components fit within the low-profile housing. In exemplary embodiments, the housing is concave to substantially conform to the cranium of a patient, and the components are arranged to fit within the concave space provided by the interior of the concave housing. In such embodiments, the radial thickness of the low-profile housing, i.e., the effective height to which the low-profile housing protrudes above the cranium, may be less than or equal to 5.2 millimeters.

A circuit board within the housing carries integrated circuits and discrete components. In some embodiments, the integrated circuits and discrete components are located on first and second opposing surfaces of the circuit board, respectively. When the implantable medical device is implanted on a cranium of a patient, the first surface and integrated circuits are oriented away from the cranium, and the second surface and discrete components are oriented towards the cranium.

In embodiments where the housing is concave, the integrated circuits and/or discrete components can be arranged on the circuit board according to height to conform to a predetermined non-linear profile, e.g., to better conform to the concavity of the housing. In particular, the integrated circuits may be arranged on the first surface of the circuit board such that the heights of the integrated circuits predominantly increase from the edges of the circuit board to the center of the circuit board. Further, the discrete components located on the second surface of the circuit board may be arranged on the second surface of the circuit board such that the heights of the integrated circuits predominantly decrease from the edges of the circuit board to the center of the circuit board. In some embodiments, the circuit board is itself concave, and may be at least partially constructed of flex tape to facilitate its concavity.

The implantable medical device may also include a telemetry coil within the housing that encircles the circuit board. The telemetry coil may be located within a different plane than the circuit board, and particularly in embodiments where the implanted medical device is implanted on a cranium may be located within a plane that is closer to the cranium than the plane of the circuit board. In some embodiments, the telemetry coil is positioned within a concave housing such that it occupies space that cannot be practically occupied by the circuit board. For example, a concave housing can include a central portion and a taper portion, and the telemetry coil can be located within the taper portion while the circuit board occupies the central potion.

In some embodiments, the implantable medical device includes a hermetic feedthrough for allowing components within the housing of the implantable medical device to be coupled to one or more electrodes, sensors, or the like located outside the housing while maintaining the hermaticity of the housing. The feedthrough may be oriented at an angle relative to a major surface of the housing. Such an orientation of the feedthrough may utilize side surfaces of a concave housing, while allowing the feedthrough to fit in a space provided within a low-profile, concave housing.

In exemplary embodiments, the implantable medical device comprises plurality of flexibly interconnected modules, and the housing comprises a housing for a control module of the implantable medical device. The control module comprises the integrated circuits and the discrete components. Other modules can include a power source module that includes a power source to provide power to the integrated circuits and the discrete components, such as a rechargeable battery, and a recharge module including a recharge coil to inductively receive energy to recharge the power source. Each module may be separately housed. The control module can include therapy delivery circuitry to generate electrical stimulation, and the implantable medical device may be an implantable neurostimulator for delivering the stimulation to the brain of a patient.

In one embodiment, the invention is directed to an implantable medical device that includes a plurality of integrated circuits, a plurality of discrete components, and a circuit board that is coupled to each of the integrated circuits and discrete components. The implantable medical device further includes a housing to house the circuit board. The circuit includes first and second surfaces. Each of the integrated circuits is located the first surface of the circuit board, and each of the discrete components is located on the second surface of the circuit board. At least one of the integrated circuits and discrete components are arranged on respective first and second surfaces to substantially conform to a predetermined non-linear profile.

In another embodiment, the invention is directed to an implantable medical device that includes a circuit board, a telemetry coil that encircles the circuit board, and a housing to house the circuit board and the telemetry coil. The circuit board is located substantially within a first plane and the telemetry coil is located substantially within a second plane. The first and second planes are substantially parallel.

In another embodiment, the invention is directed to an implantable medical device comprising a housing that includes a major surface and feedthrough that is oriented at an angle relative to the major surface.

The invention may be capable of providing one or more advantages. For example, arrangement of components of an implantable medical device according to the invention can enable a housing of the implantable medical device to have a low profile. A low-profile housing according to the invention can enable the implantable medical device to be implanted at locations within the human body for which implantation of conventional implantable medical devices is deemed undesirable. In particular, a low-profile housing may allow an implantable medical device which delivers treatment to the brain of a patient, such as implantable neurostimulator, to be implanted on the cranium of a patient rather then more remotely from the brain, such as within a subclavicular region of the patient. Consequently, the problems associated with the use of long leads needed to allow a remotely implanted medical device to access the brain may be diminished or avoided. Further, a low-profile housing, and particularly a concave, low-profile housing, may make the implantable device more comfortable and less noticeable, e.g., more cosmetically appealing, when implanted on the cranium beneath the scalp of the patient. Further, a low-profile, concave housing may make the implantable medical device more clinically acceptable by, for example, reducing the potential for skin erosion of the scalp.

The details of one or more embodiments of the invention are set forth in the accompanying drawings and the description below. Other embodiments of the invention will be apparent from the description and drawings, and from the claims.

DETAILED DESCRIPTION

Figure 1:
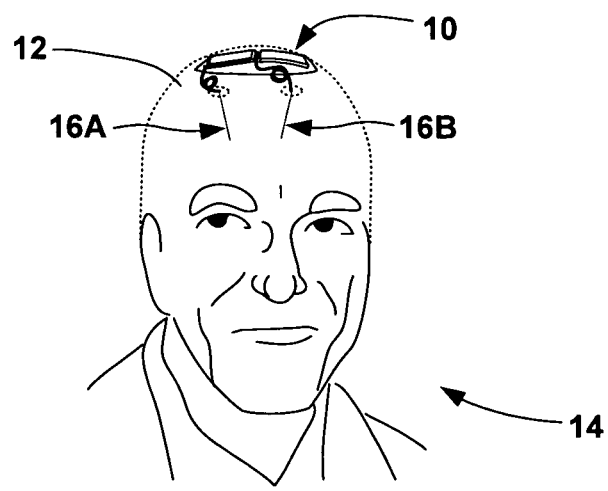
FIG. 1 is a conceptual diagram illustrating an example modular implantable medical device implanted on the cranium of a patient.

FIG. 1 is a conceptual diagram illustrating an example modular implantable medical device (IMD) 10 implanted on the cranium 12 of a patient 14. As will be described in greater detail below, IMD 10 comprises a plurality of separately housed and flexibly interconnected modules. By distributing components of IMD 10 amongst modules rather than including them within a single, rigid housing, the implantable medical device may be shaped and configured for implantation at locations within patient 14 for which implantation of conventional IMDs is deemed undesirable. Further, the flexibility of the interconnection between modules of IMD 10 may allow multiples degrees of freedom of movement between the modules, which in turn may allow the implantable medical device to conform to such areas, and in particular embodiments, to conform to surfaces within patient 14 such as the surface of cranium 12.

In the illustrated example, modular IMD 10 is coupled to two leads 16A and 16B (collectively "leads 16") that extend through holes within cranium 12, and into the brain of patient 14. In exemplary embodiments, each of leads 16 carries a plurality of electrodes, and IMD 10 delivers stimulation to the brain of patient 14 via the electrodes. Modular IMD 10 may be coupled to any number of leads 16, and in some embodiments is not coupled to any leads 16.

Because modular IMD 10 can be implanted on cranium 12 of patient 14 rather then more remotely from the brain of patient 14, such as within a subclavicular region of patient 14, the problems associated with the use of long leads needed to allow a remotely implanted IMDs to access the brain may be diminished or avoided. These problems include the requirement of tunneling under the scalp and the skin of the neck, increased surgery and recovery time, an additional procedure under general anesthesia, risk of infection or skin erosion along the track through which the leads are tunneled, and risk of lead fracture due to torsional and other forces caused by normal head and neck movements.

Figure 2:
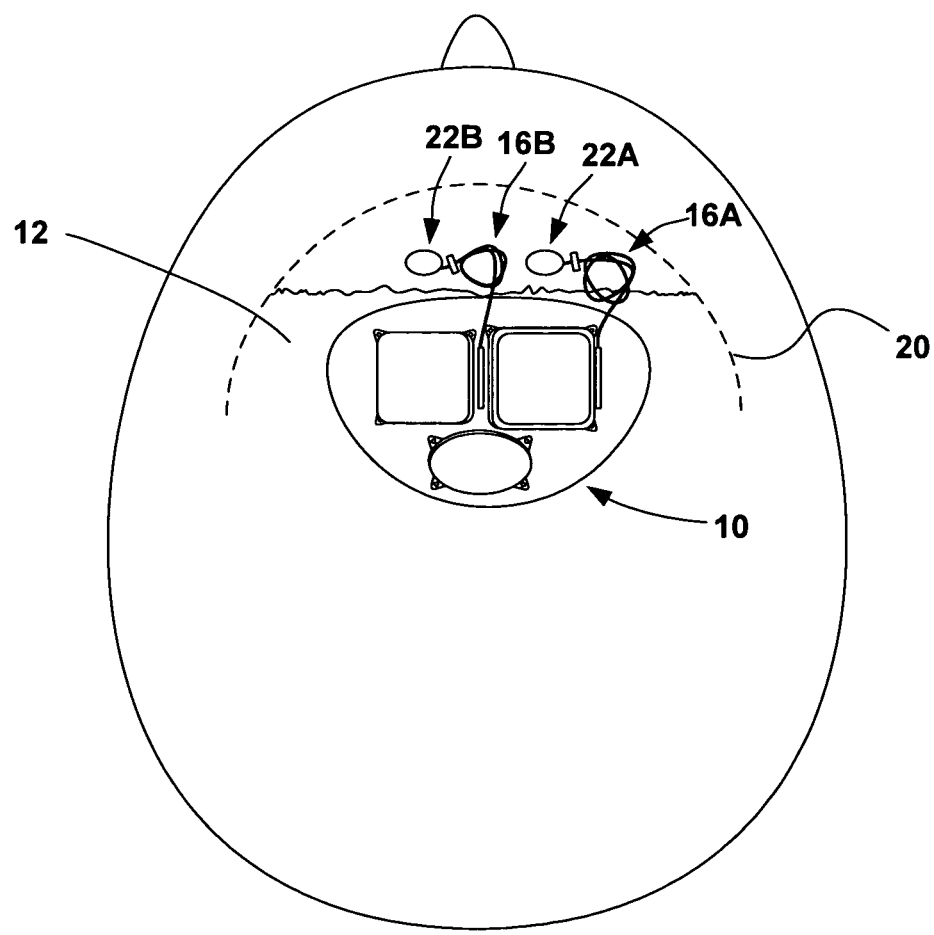
FIG. 2 is a top-view diagram further illustrating the modular implantable medical device of FIG. 1 implanted on the cranium of the patient.

FIG. 2 is a top-view diagram further illustrating modular IMD 10 implanted on cranium 12 of the patient 14. In order to implant modular IMD 10 on cranium 12, an incision 20 is made through the scalp of patient 14, and a resulting flap of skin is pulled back to expose the desired area of cranium 12. The incision may, as shown in FIG. 2, be generally shaped like a "C." Such an incision is commonly referred to as a "C-flap" incision.

Holes 22A and 22B (collectively "holes 22") are drilled through cranium 12, and leads 16 are inserted through holes 22 and into the brain of patient 14. Caps may be placed over holes 22 as is known in the art. Leads 16 are connected to modular IMD 10, either directly or via a lead extension, and modular IMD 10 is placed at least partially within a pocket formed using a hand or a tool beneath the scalp behind holes 22.

Once positioned as desired on cranium 12 within the pocket, modular IMD 10 may then be fixed to cranium 12 using an attachment mechanism such as bone screws. The skin flap may be closed over modular IMD 10, and the incision may be stapled or sutured. The location on cranium 12 at which IMD 10 is illustrated as implanted in FIG. 2 is merely exemplary, and IMD 10 can be implanted anywhere on the surface of cranium 12. Further details regarding exemplary techniques for implanting IMD 10 on the cranium may be found in a commonly-assigned U.S. patent application Ser. No. 10/731,868 entitled "IMPLANTATION OF LOW-PROFILE IMPLANTABLE MEDICAL DEVICE," which published as U.S. Patent Application Publication No. 2004/0173221 on Sep. 9, 2004.

Because of the flexibility provided by interconnect members and/or an overmold of modular IMD 10, the IMD may be manipulated during implantation such that it conforms to cranium 12. For example, in some embodiments a clinician can manipulate modular IMD 10 into conformance with cranium 12 while IMD 10 is on cranium 12 and fix modular IMD 10 into place using bone screws or the like. In other embodiments, the clinician may manipulate modular IMD 10 into conformance with cranium 12 with IMD 10 on and/or off of cranium 12, and IMD 10 may substantially retain the form into which it is manipulated.

As mentioned above, modular IMD 10 may deliver stimulation to the brain of patient 14 to, for example, provide deep brain stimulation (DBS) therapy, or to stimulate the cortex of the brain. Cortical stimulation may involve stimulation of the motor cortex. Modular IMD 10 may be used to treat any nervous system disorder including, but not limited to, epilepsy, pain, psychological disorders including mood and anxiety disorders, movement disorders (MVD), such as, but not limited to, essential tremor, Parkinson's disease and neurodegenerative disorders.

However, modular IMD 10 is not limited to delivery of stimulation to the brain of patient, and may be employed with leads 16 deployed anywhere in the head or neck including, for example, leads deployed on or near the surface of the skull, leads deployed beneath the skull such as near or on the dura mater, leads placed adjacent cranial or other nerves in the neck or head, or leads placed directly on the surface of the brain. Moreover, modular IMD 10 is not limited to implantation on cranium 12. Indeed, modular IMD 10 may be implanted anywhere within patient 14. For example, modular IMD 10 can be implanted within the neck of patient 14, and deliver stimulation to the vagus nerve or the cervical region of the spinal cord.

Modular IMD 10 may alternatively be implanted within a pectoral region or the abdomen of patient 14 to act as a diaphragmatic pacer, or to provide any of the monitoring and therapy delivery functions known in the art to be associated with cardiac pacemakers. Further, modular IMD 10 may be implanted in the upper buttock region and deliver spinal cord, urological or gastrological stimulation therapy, or may be configured to be implanted within the periphery, e.g., limbs, of patient 14 for delivery of stimulation to the muscles and/or peripheral nervous system of patient 14. As is the case with cranium 12, the modularity of IMD 10 may enable implantation at some of these example locations for which implantation of conventional IMDs is generally deemed undesirable.

Modular IMD 10 is not limited to embodiments that deliver stimulation. For example, in some embodiments modular IMD 10 may additionally or alternatively monitor one or more physiological parameters and/or the activity of patient 14, and may include sensors for these purposes. Where a therapy is delivered, modular IMD 10 may operate in an open loop mode (also referred to as non-responsive operation), or in a closed loop mode (also referred to as responsive). Modular IMD 10 may also provide warnings based on the monitoring.

As discussed above, the ability of a modular IMD 10 according to the invention to be implanted close to a region within patient 14 to be monitored enables the use of shorter leads 16. Shorter leads 16 may advantageously improve the accuracy of such sensors by reducing noise attributable to leads 16. Shorter leads 16 may also advantageously reduce the negative affects of imaging techniques such as magnetic resonance imaging "MRI" a person implanted with IMD 10.

Further, in some embodiments modular IMD 10 can additionally or alternatively deliver a therapeutic agent to patient 14, such as a pharmaceutical, biological, or genetic agent. Modular IMD 10 may be coupled to a catheter, and may include a pump to deliver the therapeutic agent via the catheter.

Figure 3:
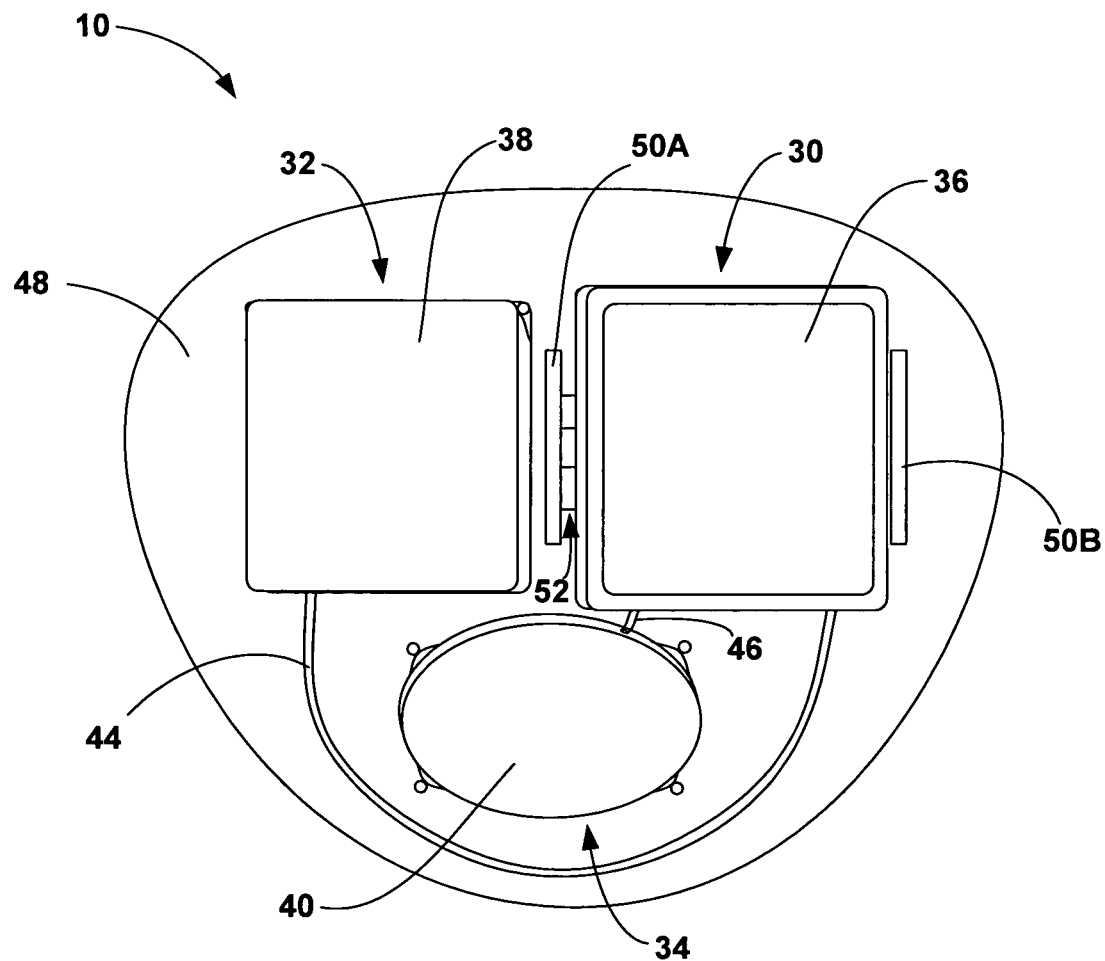
FIG. 3 is a top-view diagram further illustrating the modular implantable medical device of FIG. 1.

FIG. 3 is a top-view diagram further illustrating modular IMD 10. In the illustrated embodiment, modular IMD 10 includes three modules: a control module 30, a power source module 32, and a recharge module 34. As shown in FIG. 3, modules 30, 32 and 34 include separate housings 36, 38 and 40, respectively.

Control module 30 includes control electronics within the housing, e.g., electronics that control the monitoring and/or therapy delivery functions of modular IMD 10, such as a microprocessor. Control module 30 may also include circuits for telemetry communication with external programmers or other devices within the housing. Housing 36 of control module 30 may be hermetic in order to protect the control electronics therein, and in exemplary embodiments is formed of a rigid material, such as titanium, stainless steel, or a ceramic. In exemplary embodiments, as will be described in greater detail below, housing 36 is a low-profile, concave housing. Techniques for arranging components of control module 30 to enable such a low-profile, concave housing are also described below.

Power source module 32 includes a power source within housing 38. The power source provides power for components of other modules, such as the control electronics within control module 30. The power source may be any power source suitable for use within an IMD, such as one or more batteries, capacitors, solar cells, fuel cells, nuclear cells, or any combination thereof. In an exemplary embodiment, the power source comprises a rechargeable Lithium Ion battery, which may have a thin wound coil construction, or a foil pack or other non-coiled construction to more easily fit within housing may be less than 5 millimeters thick with an approximately one square inch surface area. Housing 38 may be hermetic, and may be formed of titanium, stainless steel, or a ceramic. Power source module 32 may include an insulator within housing 38 to isolate housing 38 from the power source.

Where the power source includes a rechargeable power, such as a rechargeable battery and/or a capacitor, modular IMD 10 may include recharge module 34. Recharge module 34 may include a recharge coil 42 within housing 40. Recharge coil 42 inductively receives energy from an external recharging unit (not illustrated) through the skin of patient 14 to recharge the power source. Recharge coil 42 may be formed of windings of copper or another highly conductive material. Housing 40 need not be hermetic, and may be formed of materials such as silicone, polymers and ceramics.

Housings 36, 38 and 40 may have any shape, including the round, coin shape and rectangular shapes with rounded edges illustrated in FIG. 3. Further, one or more surfaces of one or more of housings 36, 38 and 40 may be concave along at least one axis, and preferably two axes. Further details regarding the concavity of housings 36, 38 and 40 may be found in a commonly-assigned U.S. patent application Ser. No. 10/731,867 entitled "CONCAVITY OF AN IMPLANTABLE MEDICAL DEVICE,", which issued as U.S. Pat. No. 7,529,586 on May 5, 2009.

Modules 30, 32 and 34 can be configured in a variety of ways, and the configuration illustrated in FIG. 3 is merely exemplary. Further, modular IMD 10 can include any number of modules, and may include other types of modules instead of or in addition to a power source module 32 and a recharge module 34. For example, modular IMD 10 can include additional power source modules, modules that include additional memory that is accessible by the control electronics within control module 30, modules that include reservoirs for storing therapeutic agents and pumps for delivering therapeutic agents to patient 14, and modules that include sensors sensing physiological parameters, such as pressures or blood flows, or the activity level of patient 12. Further details regarding additional modules for and/or configurations of modules of a modular IMD may be found in a commonly-assigned U.S. patent application Ser. No. 10/731,869 entitled "MODULAR IMPLANTABLE MEDICAL DEVICE," which published as U.S. Patent Application Publication No. 2004/0176818 on Sep. 9, 2004.

Power source module 32 is coupled to control module 30 by a flexible interconnect member 44, which encloses a conductor that allows transmission of energy from the power source of power source module 32 to components such as the control electronics within control module 30. In embodiments where energy is transferred via a DC voltage on the conductor, it may be necessary to make flexible interconnect member 44 hermetic. In embodiments in which flexible interconnect member 44 is hermetic, flexible interconnect member 44 may be made of titanium or stainless steel. In embodiments where energy is transferred via a charge-balanced voltage on the conductor, such as an AC voltage, flexible interconnect member 44 need not be hermetic, and may be made of any material including silicone or various polymers.

In the illustrated embodiment, the control electronics of control module 30 regulates the recharging and discharging of the power source within power source module 32. Consequently, as shown in FIG. 3, recharge module 34 is coupled to control module 30 by a flexible interconnect member 46 that encloses a conductor that allows transmission of energy inductively received by coil 42 to control module 30. Because the energy is transferred on the conductor via a charge-balanced voltage, e.g., an AC voltage, flexible interconnect member 46 need not be hermetic, and may be made of any material including titanium, stainless steel, silicone or various polymers.

Interconnect members 44 and 46 are flexible. In some embodiments, as indicated above, interconnect members 44 and 46 are made of a flexible material such as silicone or a flexible polymer. In embodiments where flexible member 44 is hermetic and made of substantially less flexible material, such as titanium or stainless steel, the flexibility of interconnect member 44 is provided by the configuration and/or construction of flexible interconnect member 44.

Interconnect member 44 is flexible in a plurality of directions to provide modules 30 and 32 with multiple degrees of freedom of motion with respect to each other. In exemplary embodiments, interconnect member 44 provides at least three degrees of motion, and the degrees of motion provided include rotational motion. Further details regarding the configuration and/or construction of interconnect member 44 to provide such flexibility may be found in a commonly-assigned U.S. patent application Ser. No. 10/731,699 entitled "COUPLING MODULE OF A MODULAR IMPLANTABLE MEDICAL DEVICE," which issued as U.S. Pat. No. 7,848,817 on Dec. 7, 2010.

As shown in FIG. 3, modular IMD 10 includes an overmold 48, which may be flexible. In the illustrated embodiment, overmold 48 at least partially encapsulates each of housings 36, 38 and 40. Overmold 48 integrates modules 30, 32 and 34 into a desired form factor, but, where flexible, allows relative intermodule motion. In some embodiments, overmold 48 incorporates mechanical features to restrict intermodule motion to certain directions or within certain ranges. Overmold 48 may be made from silicone, and is some embodiments may be made from two or more materials of differing flexibility, such as silicone and a polyurethane. An exemplary polyurethane for this purpose is Tecothane®, which is commercially available from Hermedics Polymer Products, Wilmington, Mass. Use of the term "overmold" herein is not intend to limit the invention to embodiments in which overmold 48 is a molded structure. Overmold 48 may be a molded structure, or may be a structure formed by any process.

Overmold 48 can be shaped to contour to cranium 12, e.g., may be concave along at least one axis, and may be contoured at its edges to prevent skin erosion on the scalp of patient 14. The flexibility and shape of overmold 48 may improve the comfort and cosmetic appearance of modular IMD 10 under the scalp. Further details regarding the overmold, the concavity of the overmold, and techniques for restricting intermodular motion in a modular IMD 10 may be found in a commonly-assigned U.S. patent application Ser. No. 10/730,873 entitled "OVERMOLD FOR A MODULAR IMPLANTABLE MEDICAL DEVICE," which issued as U.S. Pat. No. 7,242,982 on Jul. 10, 2007, and a commonly-assigned U.S. patent application Ser. No. 10/731,881 entitled "REDUCING RELATIVE INTERMODULE MOTION IN A MODULAR IMPLANTABLE MEDICAL DEVICE," which issued as U.S. Pat. No. 7,392,089 on Jun. 24, 2008.

In the illustrated embodiment, modular IMD 10 also includes lead connector modules 50A and 50B (collectively "lead connector modules 50") formed within overmold 48 to receive leads 16 or lead extensions coupled to leads 16. Conductors 52 extend from lead connector modules 50 to hermetic feedthroughs (not illustrated) within housing 36 of control module 30. Lead connector modules 50 may be formed anywhere within overmold 48. In embodiments where overmold 48 includes a rigid material and a flexible material, the rigid material may form at least part of lead connector modules 50 to secure leads 16 or lead extensions, and to protect conductors 52 from damage that may result from flexing within overmold 48.

Figure 4:
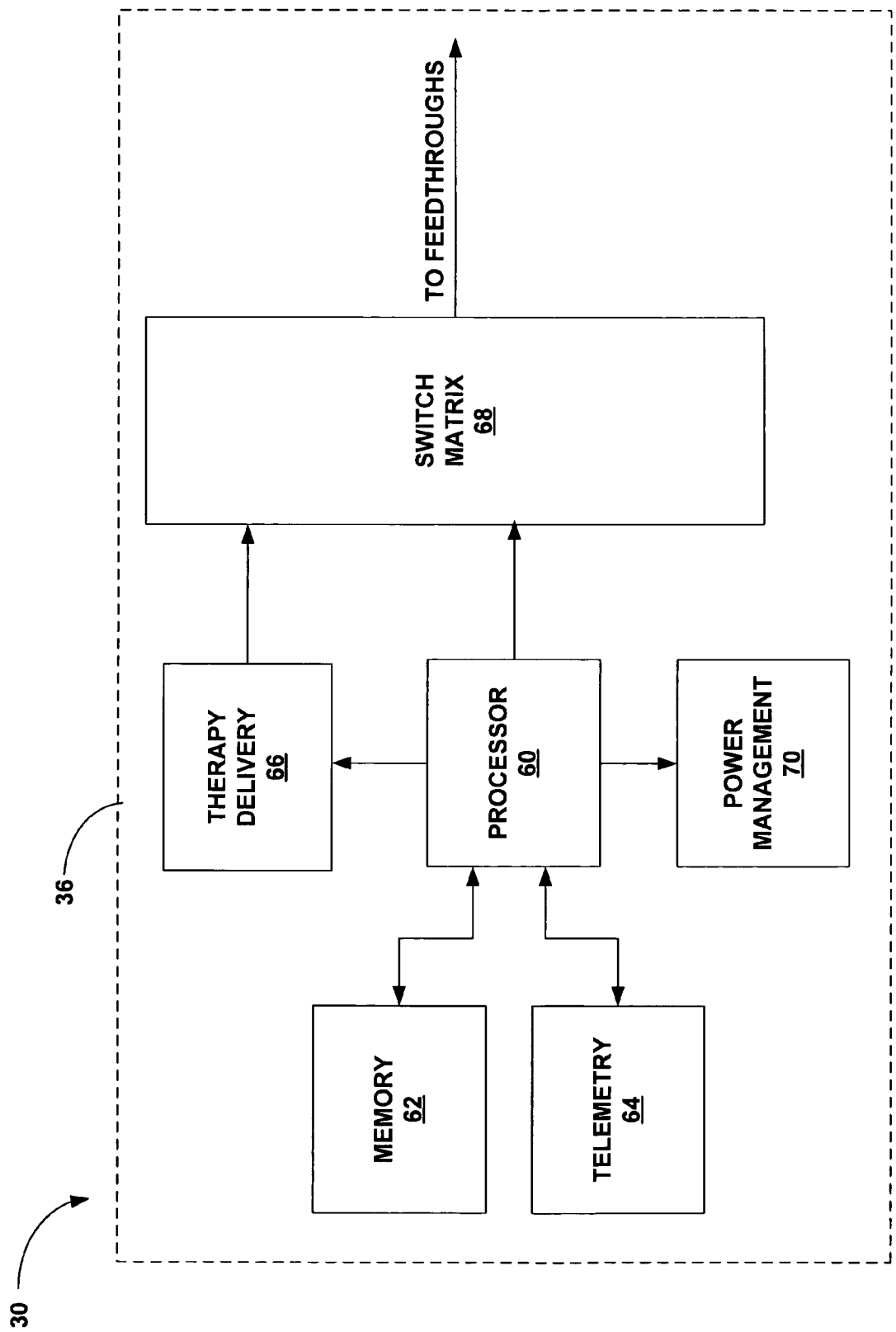
FIG. 4 is a block diagram illustrating a control module of the modular implantable medical device of FIG. 1.

FIG. 4 is a block diagram illustrating control module 30 of modular IMD 10. As described above, control module 30 includes control electronics that control the functioning of modular IMD 10 within housing 36. The control electronics include a processor 60, which may take the form of a microprocessor, digital signal processor (DSP), application specific integrated circuit (ASIC), field-programmable gate array (FPGA), or other logic circuitry.

Control module 30 also includes a memory 62, such as a read-only memory (ROM), random access memory (RAM), electronically-erasable programmable ROM (EEPROM), flash memory, or the like. Memory 62 may store program instructions that may be executed by processor 60 and thereby control the functioning of modular IMD 10. Processor 60 may also store data colleted during treatment and/or monitoring of patient 14 within memory 62.

In some embodiments, control module 30 includes telemetry circuitry 64, which enables processor 60 to communicate with other devices such as an external programming device via radio-frequency communication. Telemetry circuitry 64 may include a telemetry coil 82 (FIG. 5), which may be fabricated of windings of copper or another highly conductive material. The configuration and location of telemetry coil within housing 36 may be dictated by the available space within housing 36 as will be described in greater detail below.

In some embodiments modular IMD 10 delivers electrical stimulation, and more particularly, control module 30 includes therapy delivery circuitry 66 within housing 36 that generates electrical stimulation. In exemplary embodiments, therapy delivery circuitry 66 comprises circuits for the generation of electrical stimulation in the form of pulses, such as capacitors and switches. In embodiments in which modular IMD 10 is a neurostimulator coupled to leads 16 that include a plurality of electrodes, therapy delivery circuitry 66 may deliver the pulses to a switch matrix 68, which comprises an array of switches. In such embodiments, processor 60 interacts with switch matrix 68 to select electrodes for delivery of generated stimulation pulses. Based on the selections made by processor 60, switch matrix 68 delivers the pulses to conductors that pass through feedthroughs in housing 36 and to electrical contacts on leads 16 that are electrically coupled to the desired electrodes carried by leads 16.

The illustrated components of control module 30 receive energy from the power source within power source module 32 via interconnect member 44 (FIG. 3). In some embodiments in which the power source is rechargeable, control module 30 receives energy inductively captured by recharge module 34 via interconnect member 46, and includes power management circuitry 70 that controls the recharging and discharging of the power source. Power management circuitry 70 may ensure that the power source is not overcharged, over-discharged, or harmed. In some embodiments, power management circuitry 70 includes circuits to measure voltages, currents or temperatures associated with the power source, or rates of change of these parameters, and controls recharging and discharging according to the measured values. Power management circuitry 70 may also include circuits, such as rectifier circuits, for converting charge-balanced, e.g., AC, voltages provided by recharge coil 42 (FIG. 4) into DC voltages for recharging the power source.

Figure 5:
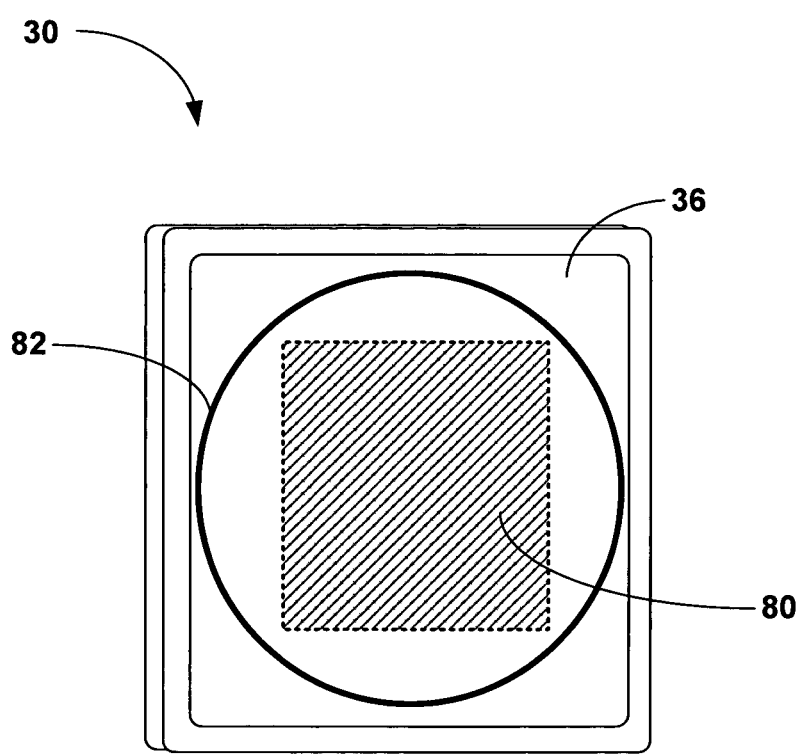
FIG. 5 top-view of a control module of the modular implantable medical device of FIG. 1.

FIG. 5 top-view of control module 30. As shown in FIG. 5, control module 30 includes a circuit board 80 and a telemetry coil 82 within housing 36. Circuit board 80 may be a multi-layer printed circuit board with substrate made of FR-5, ceramic, or other substrate materials known in the art. As discussed above, telemetry coil 82 may be formed of windings of copper or another highly conductive material.

As illustrated in FIG. 5, telemetry coil 82 is arranged within housing 36 such that it substantially encircles circuit board 80. As will be described below, in some embodiments telemetry coil 82 and circuit board 80 are arranged such that telemetry coil is located within a plane more proximate to a cranium than circuit board. Arranging telemetry coil 82 such that it substantially encircles circuit board 80 may improve inductive coupling efficiency between an external coil (not shown) and telemetry coil 82 because telemetry coil is substantially uneclipsed by circuit board 80 from the top view, which is in a direction substantially perpendicular to the plane in which the circuit board 80 and/or telemetry coil 82 are located.

Figure 6:
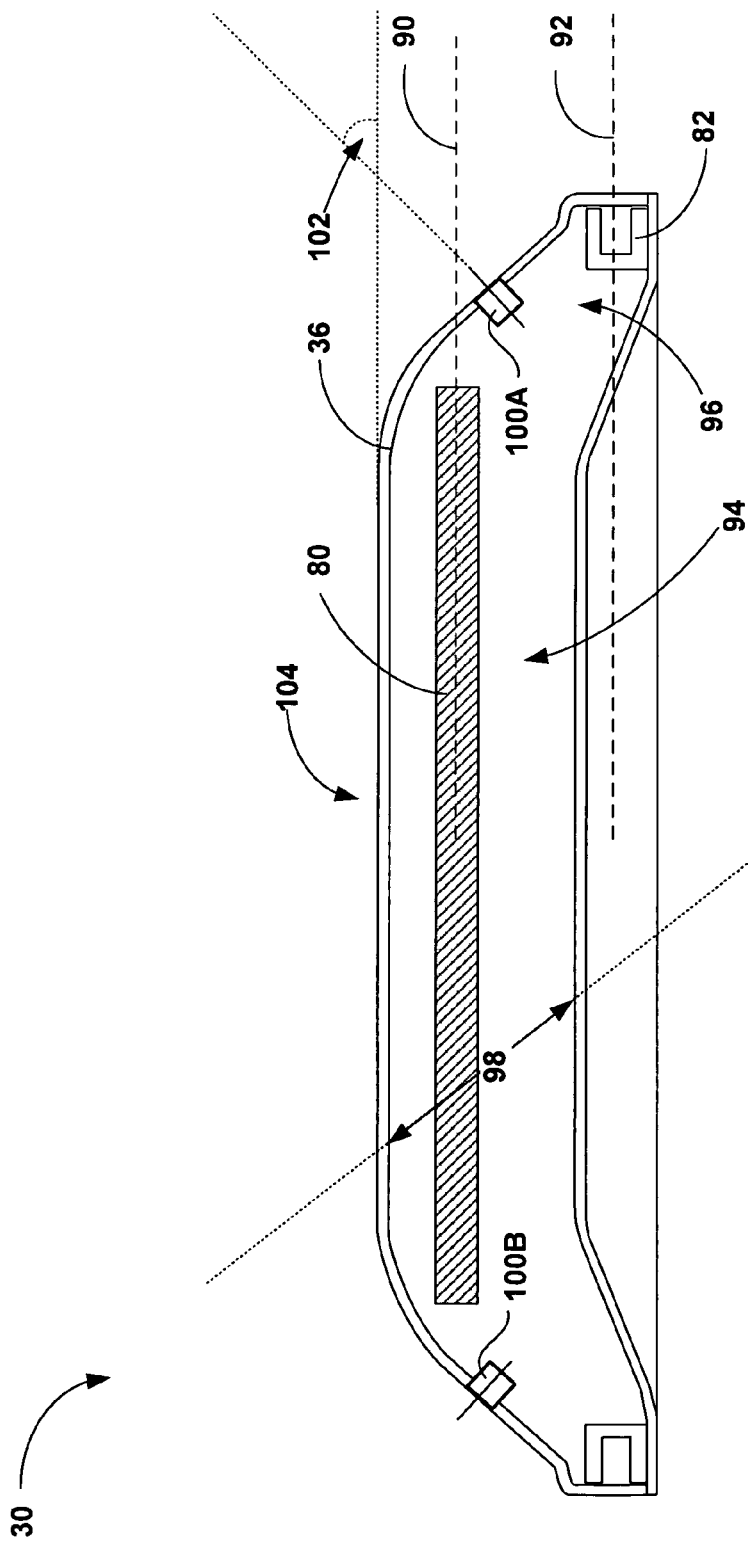
FIG. 6 is a cross-sectional view of the control module of the modular implantable medical device of FIG. 1.

FIG. 6 is a cross-sectional view of control module 30. As shown in FIG. 6, circuit board is within a first plane 90, and telemetry coil is located within a second plane 92 that is different than first plane 90. Planes 90 and 92 may, as shown in FIG. 6, be substantially parallel. Further, second plane 92 be located below first plane 90, e.g., may located closer to cranium 12 of patient 14 when modular IMD 10 is implanted on cranium 12.

In some embodiments it is desirable for housing 36 to have a concave shape such as that illustrated in FIG. 6. The concavity of housing 36 and associated advantages are described in greater detail in a commonly-assigned U.S. patent application Ser. No. 10/731,867 entitled "CONCAVITY OF AN IMPLANTABLE MEDICAL DEVICE,", which issued as U.S. Pat. No. 7,529,586 on May 5, 2009. In such embodiments, the interior of housing 36 may include a larger central portion 94 and a smaller taper portion 96

Hybrid circuit board 80 may be sized such that it must be located within central portion 94. In order to minimize the size of central portion 94 and utilize the volume within taper portion 96, telemetry coil 82 may be located within taper portion 96. In some embodiments, circuit board may be at least partially constructed of flex tape, and may be concave in one or more axes to better conform to the concavity of housing 36.

By configuring housing 36, circuit board 80 and telemetry coil 82 as illustrated, a radial thickness 98 of housing 36 may be less than or equal to 5.2 millimeters. Thickness 98 may be approximately the effective height to which housing 36 protrudes from the surface of cranium 12 when implanted thereon.

In some embodiments, housing 36 includes one or more hermetic feedthroughs, such as feedthroughs 100A and 100B (collectively "feedthroughs 100") that allow components within housing 36 to be coupled to one or more electrodes, sensors, or the like located outside housing 36 while maintaining the hermaticity housing 36. Feedthroughs 100 may, as shown if FIG. 6, be oriented at a angle 102 relative to a major surface, e.g., the top 104 or the bottom of the housing. Angle 102 is between 0 and 90 degrees, and in exemplary embodiments, angle 102 is approximately equal to 45 degrees. Where housing 36 is concave as shown in FIG. 6, feedthroughs 100 may be oriented along a radius of housing 36. Such an orientation of the feedthroughs 100 may utilize side surfaces of a concave housing 36, while allowing the feedthrough 100 to fit in a space provided within housing 36. Further, by orienting feedthroughs 100 at angle 102, the contribution of feedthroughs 100 to the height and width of housing 36 may be reduced.

Figure 7:
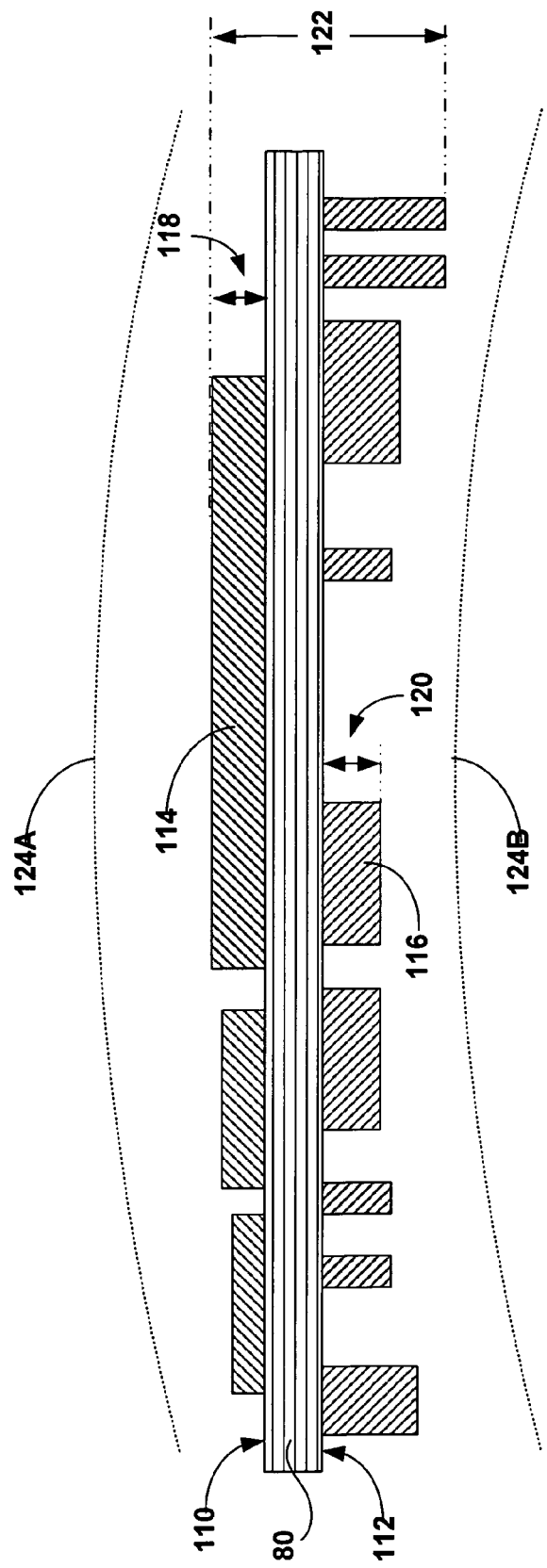
FIG. 7 is a cross-sectional view of a circuit of the control module of FIG. 6.

FIG. 7 is a cross-sectional view of circuit board 80. Hybrid circuit board 80 includes a first side 110 and a second side 112. Integrated circuits 114 are coupled to circuit board 80, and are located on first side 110. Discrete components 116, such as capacitors, resistors, diodes, discrete switches, inductors, and transformers are also coupled to circuit board 80, and are located on second side 112. Combinations of integrated circuits 114 and/or discrete components 116 form the various components 60-70 of control module 30 illustrated in block diagram form in FIG. 4. For example, processor 60 may include one or more integrated circuits 114. For ease of illustration, only a single integrated circuit 114 and single discrete component 116 are labeled.

Each of integrated circuits 114 have a height 118, and each of discrete components 116 have a height 120. Generally, heights 120 of discrete components 116 are greater than heights 118 of integrated circuits 114. By grouping all of integrated circuits 114 together on first side 110, and all of discrete components 116 together on second side 112, the overall thickness 122 of circuit board 80 including integrated circuits 114 and discrete components 116 can be reduced. Further reduction in thickness 122 may be achieved by replacing large value discrete components, such as high capacitance capacitors, with parallel lower-value components. Thickness 122 may be less than or equal to 3.8 millimeters.

In embodiments in which housing 36 is concave as shown in FIG. 6, the area above circuit board 80 may be smaller than that below circuit board 80. In such embodiments, because the areas of integrated circuits 114 are less than the areas of discrete components 116, circuit board 80 may be oriented within housing 36 such that second side 112 and discrete components 116 face "downward," e.g., toward cranium 12 when modular IMD 10 is implanted thereon, and first side 110 and integrated circuits 114 face "upward," e.g., away from cranium 12 when modular IMD 10 is implanted thereon.

Integrated circuits 114 and discrete components 116 may be arranged on circuit board 80 such that their heights 118, 120 substantially conform to a predetermined non-linear profile. In the illustrated example, in order to conform to the concavity of housing 36 represented by arcs 124A and 124B, integrated circuits 114 may, as shown in FIG. 6, be arranged on first side 110 such that the heights 118 of integrated circuits 114 predominantly increase from the edges to the center of first side 110. The heights 120 of discrete components 116, on the other hand, may as shown in FIG. 6 predominantly decrease from the edges to the center of second side 112.

Various embodiments of the invention have been described. However, one skilled in the art will appreciate that the invention is not limited to the described embodiments, and that modification may be made to the described embodiments without departing from the scope of the claims. For example, although described herein in the context of a modular IMD including flexibly interconnect modules and an overmold, the invention is not so limited. In some embodiments, the interconnections between modules of an IMD are not flexible. Moreover, in some embodiments, an IMD comprises a single low-profile housing with a circuit board and telemetry coil arranged as described herein. These and other embodiments are within the scope of the following claims.

The invention claimed is:

1. An implantable medical device comprising:
a plurality of integrated circuits;
a plurality of discrete components;
a circuit board that is coupled to each of the integrated circuits and discrete components;
and a housing to house the circuit board,
wherein the circuit board comprises first and second opposing surfaces, the housing houses the first and second surfaces, each of the integrated circuits is located on the first surface, and each of the discrete circuit components is located on the second surface,
wherein at least one of the integrated circuits or discrete components are arranged on the respective one of the first or second surfaces to substantially conform to a first predetermined non-linear profile that is based on a second non-linear profile of the housing, and
wherein each of the discrete components has a height, and the discrete components are arranged on the second surface of the circuit board such that the heights of the discrete components predominantly decrease from an edge of the second surface of the circuit board to a center of the second surface of the circuit board.

2. An implantable medical device comprising:
a plurality of integrated circuits;

a plurality of discrete components;
a circuit board that is coupled to each of the integrated circuits and discrete components; and
a housing to house the circuit board,
wherein the circuit board comprises first and second opposing surfaces, the housing houses the first and second surfaces, each of the integrated circuits is located on the first surface, and each of the discrete circuit components is located on the second surface,
wherein at least one of the integrated circuits or discrete components are arranged on the respective one of the first or second surfaces to substantially conform to a first predetermined non-linear profile that is based on a second non-linear profile of the housing, and
wherein a thickness of the circuit board including the integrated circuits and the discrete components is less than or equal to 3.8 millimeters.

3. An implantable medical device comprising:
a plurality of integrated circuits;
a plurality of discrete components;
a circuit board that is coupled to each of the integrated circuits and discrete components; and
a housing to house the circuit board,
wherein the circuit board comprises first and second opposing surfaces, the housing houses the first and second surfaces, each of the integrated circuits is located on the first surface, and each of the discrete circuit components is located on the second surface,
wherein at least one of the integrated circuits or discrete components are arranged on the respective one of the first or second surfaces to substantially conform to a first predetermined non-linear profile that is based on a second non-linear profile of the housing, and
wherein a radial thickness of the housing is less than or equal to 5.2 millimeters.

4. An implantable medical device comprising:
a circuit board;
a telemetry coil that encircles the circuit board;
a housing to house the circuit board and the telemetry coil, wherein the circuit board is located substantially within a first plane and the telemetry coil is located substantially within a second plane that is different than the first plane, the first and second planes are substantially parallel, and the telemetry coil is substantially uneclipsed by the circuit board in a direction substantially perpendicular to at least one of the first or second planes;
a plurality of integrated circuits; and
a plurality of discrete components, wherein the integrated circuits and discrete components are coupled to the circuit board, and a thickness of the circuit board including the integrated circuits and discrete components is less than or equal to 3.8 millimeters.

5. An implantable medical device comprising:
a circuit board;
a telemetry coil that encircles the circuit board; and
and a housing to house the circuit board and the telemetry coil,
wherein the circuit board is located substantially within a first plane and the telemetry coil is located substantially within a second plane that is different than the first plane, the first and second planes are substantially parallel, and the telemetry coil is substantially uneclipsed by the circuit board in a direction substantially perpendicular to at least one of the first or second planes, and
wherein a radial thickness of the housing is less than or equal to 5.2 millimeters.

6. The implantable medical device of claim 1, wherein the implantable medical device is configured such that when the implantable medical device is implanted on the cranium such that the first surface is oriented away from a cranium of a patient, the second surface is oriented toward the cranium.

7. The implantable medical device 1, further comprising a telemetry coil within the housing that encircles the circuit board.

8. The implantable medical device 7, wherein the telemetry coil is substantially uneclipsed by the circuit board.

9. The implantable medical device of claim 7, wherein the circuit board is located substantially within a first plane and the telemetry coil is located substantially within a second plane, and the first and second planes are substantially parallel.

10. The implantable medical device of claim 9, wherein the housing is configured to be implanted on a surface of a cranium of a patient such that the second plane is located closer to the surface of the cranium of the patient than the first plane when the implantable medical device is implanted on the cranium such that the second surface of the circuit board is oriented closer to the cranium than the first surface.

11. The implantable medical device of claim 7, wherein the housing includes a central portion and a taper portion, the circuit board is located within the central portion, and the telemetry coil is located within the taper portion.

12. The implantable medical device of claim 1, wherein the first predetermined non-linear profile comprises the second profile of the housing.

13. The implantable medical device of claim 1, wherein a thickness of the circuit board including the integrated circuits and the discrete components is less than or equal to 3.8 millimeters.

14. The implantable medical device of claim 1, wherein a radial thickness of the housing is less than or equal to 5.2 millimeters.

15. The implantable medical device of claim 1, wherein the circuit board is substantially concave along at least one axis.

16. The implantable medical device of claim 15, wherein the circuit board comprises flex tape.

17. The implantable medical device of claim 1, wherein the housing comprises a feedthrough on a side surface that is oriented at a non-parallel, non-perpendicular angle relative to a major surface of the housing.

18. The implantable medical device of claim 17, wherein the angle is approximately equal to 45 degrees.

19. The implantable medical device of claim 17, wherein the feedthrough is oriented substantially along a radius of the housing.

20. The implantable medical device of claim 1, wherein the housing comprises a first housing, the implantable medical device further comprising a second housing that houses a power source that provides power to the integrated circuits and the discrete components.

21. The implantable medical device of claim 1, wherein implantable medical device comprises an implantable neurostimulator.

22. The implantable medical device of claim 21, wherein the implantable medical device is adapted to deliver stimulation to a brain of a patient.

23. The implantable medical device of claim 1, wherein the second non-linear profile of the housing is substantially concave along at least one axis.

24. The implantable medical device of claim 2, further comprising a telemetry coil within the housing that encircles the circuit board.

25. The implantable medical device 24, wherein the telemetry coil is substantially uneclipsed by the circuit board.

26. The implantable medical device of claim 24, wherein the circuit board is located substantially within a first plane and the telemetry coil is located substantially within a second plane, and the first and second planes are substantially parallel.

27. The implantable medical device of claim 24, wherein the housing includes a central portion and a taper portion, the circuit board is located within the central portion, and the telemetry coil is located within the taper portion.

28. The implantable medical device of claim 2, wherein the first predetermined non-linear profile comprises the second profile of the housing.

29. The implantable medical device of claim 2, wherein each of the integrated circuits has a height, and the integrated circuits are arranged on the first surface of the circuit board such that the heights of the integrated circuits predominantly increase from an edge of the first surface of the circuit board to a center of the first surface of the hybrid circuit board.

30. The implantable medical device of claim 2, wherein a radial thickness of the housing is less than or equal to 5.2 millimeters.

31. The implantable medical device of claim 2, wherein the circuit board is substantially concave along at least one axis.

32. The implantable medical device of claim 2, wherein the housing comprises a feedthrough on a side surface that is oriented at a non-parallel, non-perpendicular angle relative to a major surface of the housing.

33. The implantable medical device of claim 2, wherein the housing comprises a first housing, the implantable medical device further comprising a second housing that houses a power source that provides power to the integrated circuits and the discrete components.

34. The implantable medical device of claim 2, wherein implantable medical device comprises an implantable neurostimulator.

35. The implantable medical device of claim 2, wherein the second non-linear profile of the housing is substantially concave along at least one axis.

36. The implantable medical device of claim 3, further comprising a telemetry coil within the housing that encircles the circuit board.

37. The implantable medical device 36, wherein the telemetry coil is substantially uneclipsed by the circuit board.

38. The implantable medical device of claim 36, wherein the circuit board is located substantially within a first plane and the telemetry coil is located substantially within a second plane, and the first and second planes are substantially parallel.

39. The implantable medical device of claim 36, wherein the housing includes a central portion and a taper portion, the circuit board is located within the central portion, and the telemetry coil is located within the taper portion.

40. The implantable medical device of claim 3, wherein the first predetermined non-linear profile comprises the second profile of the housing.

41. The implantable medical device of claim 3, wherein each of the integrated circuits has a height, and the integrated circuits are arranged on the first surface of the circuit board such that the heights of the integrated circuits predominantly increase from an edge of the first surface of the circuit board to a center of the first surface of the hybrid circuit board.

42. The implantable medical device of claim 3, wherein the circuit board is substantially concave along at least one axis.

43. The implantable medical device of claim 3, wherein the housing comprises a feedthrough on a side surface that is oriented at a non-parallel, non-perpendicular angle relative to a major surface of the housing 44. The implantable medical device of claim 3, wherein the housing comprises a first housing, the implantable medical device further comprising a second housing that houses a power source that provides power to the integrated circuits and the discrete components.

45. The implantable medical device of claim 3, wherein implantable medical device comprises an implantable neurostimulator.

46. The implantable medical device of claim 3, wherein the second non-linear profile of the housing is substantially concave along at least one axis.

47. The implantable medical device of claim 4, wherein the housing comprises a substantially concave portion and is configured to be implanted on a surface of a cranium of a patient such that the second plane is located closer to the surface of the cranium of the patient than the first plane when the medical device is implanted on the cranium such that the substantially concave portion of the housing substantially conforms to the surface of the cranium.

48. The implantable medical device of claim 4, wherein the housing is substantially concave in two axes and includes a central portion and a taper portion, the circuit board is located within the central portion, and the telemetry coil is located within the taper portion.

49. The implantable medical device of claim 4, wherein a radial thickness of the housing is less than or equal to 5.2 millimeters.

50. The implantable medical device of claim 4, wherein the circuit board is substantially concave along at least one axis.

51. The implantable medical device of claim 4, wherein the circuit board comprises flex tape.

52. The implantable medical device of claim 4, wherein the housing comprises a first housing, the implantable medical device further comprising a second housing that houses a power source that provides power to the circuit board.

53. The implantable medical device of claim 4, wherein implantable medical device comprises an implantable neurostimulator.

54. The implantable medical device of claim 53, wherein the implantable medical device is adapted to deliver stimulation to a brain of a patient.

55. The implantable medical device of claim 5, wherein the housing comprises a substantially concave portion and is configured to be implanted on a surface of a cranium of a patient such that the second plane is located closer to the surface of the cranium of the patient than the first plane when the medical device is implanted on the cranium such that the substantially concave portion of the housing substantially conforms to the surface of the cranium.

56. The implantable medical device of claim 55, wherein the housing is substantially concave in two axes and includes a central portion and a taper portion, the circuit board is located within the central portion, and the telemetry coil is located within the taper portion.

57. The implantable medical device of claim 5, wherein the circuit board is substantially concave along at least one axis.

58. The implantable medical device of claim 5, wherein the circuit board comprises flex tape.

59. The implantable medical device of claim 5, wherein the housing comprises a first housing, the implantable medical device further comprising a second housing that houses a power source that provides power to the circuit board.

60. The implantable medical device of claim 5, wherein implantable medical device comprises an implantable neurostimulator.

* * * * *

UNITED STATES PATENT AND TRADEMARK OFFICE
CERTIFICATE OF CORRECTION

| | | |
|---|---|---|
| PATENT NO. | : 8,457,744 B2 | Page 1 of 1 |
| APPLICATION NO. | : 10/730877 | |
| DATED | : June 4, 2013 | |
| INVENTOR(S) | : Janzig et al. | |

It is certified that error appears in the above-identified patent and that said Letters Patent is hereby corrected as shown below:

In the Claims:

Col. 13, Line 56: "circuit board; and and a housing" should read --circuit board; and a housing--

Col. 14, Line 6: "implantable medical device 1" should read --implantable medical device of claim 1--

Col. 14, Line 9: "implantable medical device 9" should read --implantable medical device of claim 9--

Col. 15, Line 44: "implantable medical device 36" should read --implantable medical device of claim 36--

Col. 16, Line 2: "surface of the housing" should read --surface of the housing.--

Signed and Sealed this
Eighth Day of October, 2013

Teresa Stanek Rea
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,457,744 B2 | Page 1 of 1 |
| APPLICATION NO. | : 10/730877 | |
| DATED | : June 4, 2013 | |
| INVENTOR(S) | : Janzig et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1437 days.

Signed and Sealed this
Thirtieth Day of December, 2014

Michelle K. Lee
*Deputy Director of the United States Patent and Trademark Office*